United States Patent [19]

Ganguly et al.

[11] Patent Number: 5,286,259
[45] Date of Patent: * Feb. 15, 1994

[54] DUAL-DIAMETER MULTIFUNCTION CATHETER

[75] Inventors: Dipankar Ganguly, Redmond; Faina Pulvermakher, Bellevue, both of Wash.

[73] Assignee: Diagnostic Devices Group Limited, Kirkland, Wash.

[*] Notice: The portion of the term of this patent subsequent to Apr. 28, 2009 has been disclaimed.

[21] Appl. No.: 837,724

[22] Filed: Feb. 18, 1992

Related U.S. Application Data

[63] Continuation of Ser. No. 494,109, Mar. 15, 1990, Pat. No. 5,108,369.

[51] Int. Cl.$^5$ .............................................. A61M 29/00
[52] U.S. Cl. ..................................... 604/96; 604/104; 604/280; 606/192; 606/194
[58] Field of Search ..................... 604/40, 43, 93, 53, 604/96–104, 158, 258, 264, 280, 283; 606/191–194; 128/660.02, 661.04, 661.08

[56] References Cited

U.S. PATENT DOCUMENTS

| 3,995,623 | 12/1976 | Blake et al. | 604/96 |
|---|---|---|---|
| 4,327,720 | 5/1982 | Bronson et al. | 604/96 |
| 4,721,115 | 1/1988 | Owens | 604/96 |
| 4,795,439 | 1/1989 | Guest | 604/43 |
| 4,802,490 | 2/1989 | Johnston | 604/96 |
| 4,817,624 | 4/1989 | Newbower | 128/692 |
| 4,856,529 | 8/1989 | Segal | 128/661 |
| 4,878,495 | 11/1989 | Grayzel | 128/344 |
| 4,878,898 | 11/1989 | Griffin et al. | 604/101 |
| 4,883,459 | 11/1989 | Calderon | 604/28 |
| 4,930,496 | 6/1990 | Bosley, Jr. | 128/24 |
| 4,954,129 | 9/1990 | Giuliani et al. | 604/53 |
| 5,010,886 | 4/1991 | Passafaro et al. | 128/660.03 |
| 5,108,369 | 4/1992 | Ganguly et al. | 604/96 |

FOREIGN PATENT DOCUMENTS

| 2262220A | 6/1987 | European Pat. Off. | 604/96 |
|---|---|---|---|
| 0303756 | 2/1989 | European Pat. Off. | |
| 0418147 | 3/1991 | European Pat. Off. | |

Primary Examiner—C. Fred Rosenbaum
Assistant Examiner—Chalin Smith
Attorney, Agent, or Firm—Christensen, O'Connor, Johnson & Kindness

[57] ABSTRACT

A catheter (10) is disclosed having a stepped coaxial construction formed by and internal tube (12) and an external tube (14). The internal tube includes a distal pressure lumen (26), a balloon inflation lumen (28), and a sensor lumen (30). The external tube includes the first proximal pressure lumen (48), second proximal pressure lumen (50), injection lumen (52), and transducer lead lumen (54). A cylindrical transducer (16), sensor (18), and balloon (42) are supported on the internal and external tubes, which allow the transducer to be coaxially mounted thereon. The catheter has a high lumen count, large lumen cross-sectional area, is easy to construct and use, and allows cardiac output to be measured continuously without sacrificing other currently available catheter functions.

5 Claims, 5 Drawing Sheets

DUAL-DIAMETER MULTIFUNCTION CATHETER

This is a continuation of the prior application Ser. No. 07/494,109 filed Mar. 15, 1990, the benefit of the filing date of which is hereby claimed under 35 U.S.C. § 120 now U.S. Pat. No. 5,108,369.

FIELD OF THE INVENTION

This invention relates generally to catheters and, more particularly, to catheters having a dual-diameter construction.

BACKGROUND OF THE INVENTION

Catheters have long been used in the medical field to invasively obtain patient information and administer treatment. A conventional catheter is an elongate tube having a distal end and a proximal end. The distal end is designed for insertion into a fluid-filled passageway or cavity in the patient, such as one of the various intravascular conduits. The proximal end of the catheter remains outside of the patient and is provided with a termination assembly accessible to the health care provider. In this manner, the catheter provides a communication link between the patient's fluid-filled passageway or cavity and the health care provider for diagnosis and treatment.

Typically, the catheter includes one or more axial conduits known as lumens extending between the distal and proximal ends of the catheter. These lumens may contain, for example, electrical wires or optical fibers that transmit information between sensors located at the distal end of the catheter and bedside instruments at the proximal end of the catheter. The operation of the sensors is controlled and their outputs interpreted by the bedside instruments, allowing the sensor/catheter/instrument system to be used for monitoring and diagnosis.

Other lumens may extend between the termination assembly and ports provided at various points along the catheter, placing the termination assembly of the catheter in fluid communication with those ports. As a result, characteristics of fluids in the patient passageway can be monitored and additional therapeutic fluids can be introduced by the health car provider.

One application in which catheters have been extensively used is the determination of volumetric flow rate in an intravascular conduit. In that regard, several catheter-based techniques have been developed to determine a patient's cardiac output, i.e., the volumetric flow rate of blood in the patient's pulmonary artery.

The first of these approaches is conventionally termed the "thermal dilution" method. Under this approach, a bolus of cold solution is introduced into one of several lumens in a multiple-lumen catheter, via the termination assembly. The cold solution then enters the intravascular conduit through a port at the end of the lumen and on the exterior of the catheter. A thermistor located on the distal, downstream end of the catheter is coupled to the termination assembly by wires positioned in another lumen. The "dilution" of, or change in, blood temperature at the thermistor with time is then measured by an instrument coupled to the termination assembly. The resultant thermal change is electronically interpreted and cardiac output computed therefrom.

Thermal dilution techniques also typically employ an inflatable segment or balloon at the distal end of the catheter. This balloon is coupled to the termination assembly by yet another lumen in the catheter. The balloon can, thus, be controllably inflated by the health care provider and used as a flotation device to facilitate positioning of the catheter in the pulmonary artery.

The thermal dilution method does, however, have certain disadvantages. For example, this technique has proved to be of limited accuracy. In addition, cumbersome apparatus are required to provide the bolus and only intermittent information can be obtained.

Another approach to the measurement of cardiac output involves the use of ultrasonic energy. Unlike the thermal dilution method discussed above, ultrasonic techniques can provide cardiac output measurements continuously. This is of considerable value in the treatment of critically ill patients whose cardiac functions may change abruptly.

Ultrasonic techniques involve the use of a transducer positioned close to the distal end of the catheter. This transducer is connected to the termination assembly at the proximal end of the catheter by electrical wires threaded through one of the catheter lumens. A bedside monitor attached to the termination assembly applies a high-frequency electrical signal (typically in the megaHertz range) to the transducer, causing it to emit ultrasonic energy. Some of the emitted ultrasonic energy is then reflected by the blood cells flowing past the catheter and returned to the transducer. This reflected and returned energy is shifted in frequency in accordance with the Doppler phenomenon.

The transducer converts the Doppler-shifted, returned ultrasonic energy to an output electrical signal. This output electrical signal is then received by the bedside monitor via the lumen wiring and is used to quantitatively detect the amplitude and frequency-shifted Doppler signal associated with the ultrasonic energy reflected from the moving blood cells.

Existing ultrasonic measurement systems process the amplitude and frequency shift information electronically to estimate the average velocity of the blood flowing through the conduit in which the transducer-carrying catheter is inserted. Such systems also require that an independent estimation of the cross-sectional area of the conduit be made using one of a variety of techniques taught in the literature, including, for example, the approach disclosed in U.S. Pat. No. 4,802,490. Cardiac output is then computed by multiplying the average velocity and cross-sectional area estimates.

One particular method of generating and processing ultrasonic signals for use in cardiac output determination employs a cylindrical transducer. The transducer is mounted coaxially on a catheter suitable for insertion into the pulmonary artery. As will be appreciated, there is, thus, a need for a catheter capable of carrying a cylindrical ultrasound transducer. Furthermore, in order to enhance the clinical utility of such a catheter, the catheter should retain some or all of the clinical functions already available through nonultrasonic catheters. Such a multifunction catheter would, however, be subject to a variety of design constraints.

Specifically, the catheter must have a small diameter for insertion into the particular conduit of interest and to minimize trauma to the patient at both the point of entry and along the inside region of the conduit in which it is inserted. Furthermore, the catheter should be designed so that the transducer does not significantly alter the catheter's diameter, thereby minimizing flow occlusion, thrombus formation and other mechanical traumas.

The catheter should also have a high lumen count, in other words, a relatively large number of independent lumens, so that several types of information can be collected and a variety of treatments performed. In addition, the lumens should have relatively large cross sections, especially when they are employed to measure pressures via a fluid connection between the distal and proximal ends of the catheter. The construction of a catheter having a small diameter, however, is in direct conflict with the provision of a high lumen count and large lumen crosssection.

The flexibility of the catheter should also be designed to provide an optimal balance between the catheter's maneuverability through tortuous passageways and its tendency to kink and fold. Furthermore, it is essential that the flexibility be uniform over the length of the catheter to further reduce the probability of kinking due to the forces applied on flexible sections of the catheter by other, relatively inflexible, sections during insertion.

Finally, because catheters are used invasively, they are conventionally disposed of after a single use. Thus, it is desirable to keep the catheter's unit cost as low as possible. For that reason, the construction of the catheter should be simple and involve a minimum expense. Further, the electrical and mechanical coupling of a transducer to the catheter should be straightforward.

In view of the preceding remarks, it would be desirable to provide a small-diameter multifunction catheter that is capable of carrying a coaxially mounted ultrasound transducer that has a high lumen count and large lumen cross-sectional area, and that is uniformly flexible and easy to construct.

SUMMARY OF THE INVENTION

In accordance with this invention, a catheter is provided including an external tube and an internal tube. The external tube has proximal and distal ends and is provided with a primary lumen and a plurality of secondary lumens. The primary lumen is roughly circular in cross section and each of the secondary lumens roughly defines a segment of an annulus in cross section. The internal tube also has proximal and distal ends and is provided with a plurality of inner tube lumens. Each inner tube lumen roughly defines a circular sector in cross section. The internal tube is receivable within the primary lumen of the external tube.

In accordance with another aspect of this invention, the catheter includes an ultrasound transducer attached adjacent the distal end of the external tube. A coaxial cable, receivable within one of the secondary lumens, is connectable to the ultrasound transducer. The internal tube is further made of a first material having a hardness of Shore D65 and the external tube is made of a second material having a hardness of Shore A93. Thus, the internal tube is relatively rigid and the external tube is relatively flexible.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
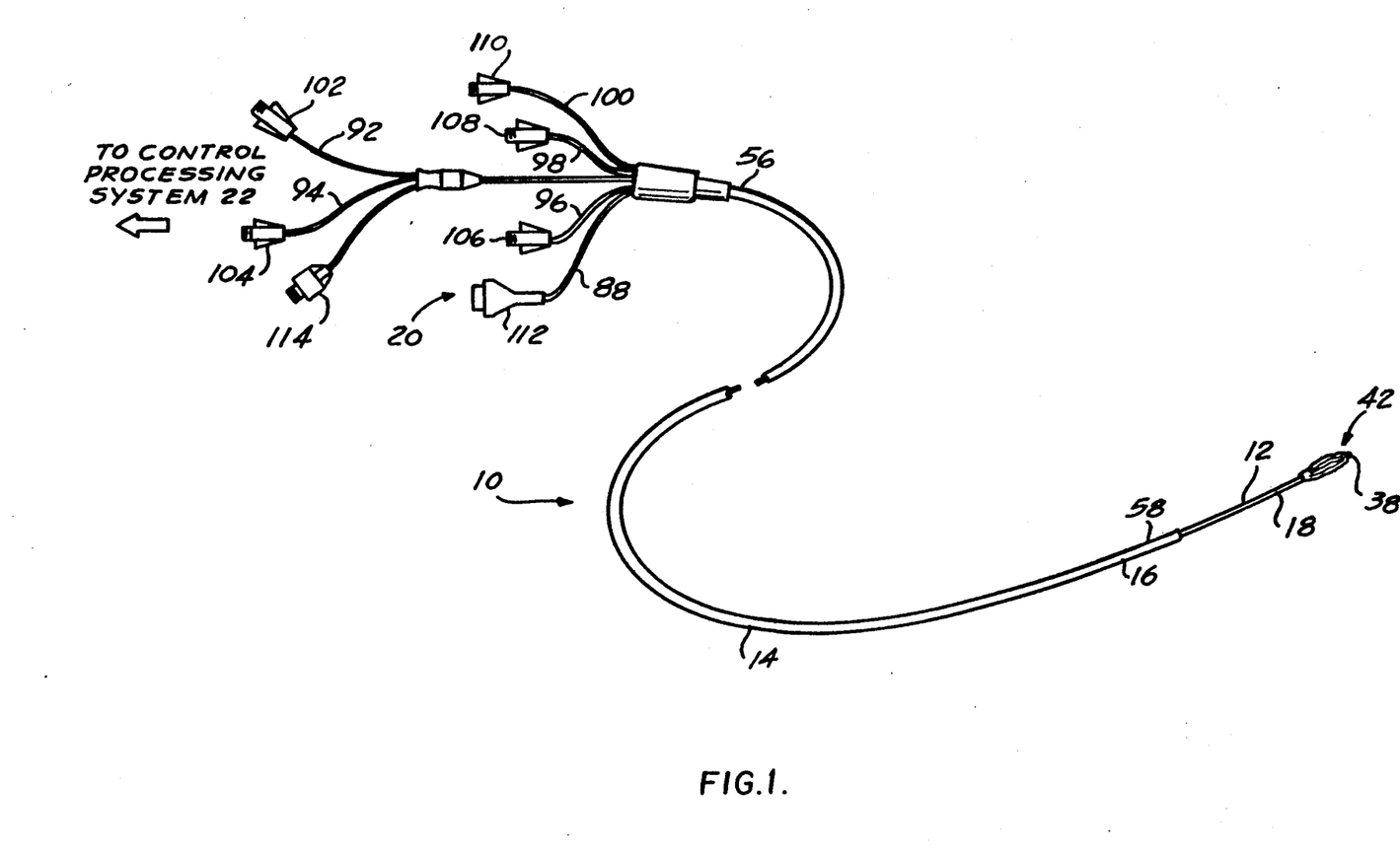
FIG. 1 is an isometric view of a catheter constructed in accordance with this invention.
Figure 2:
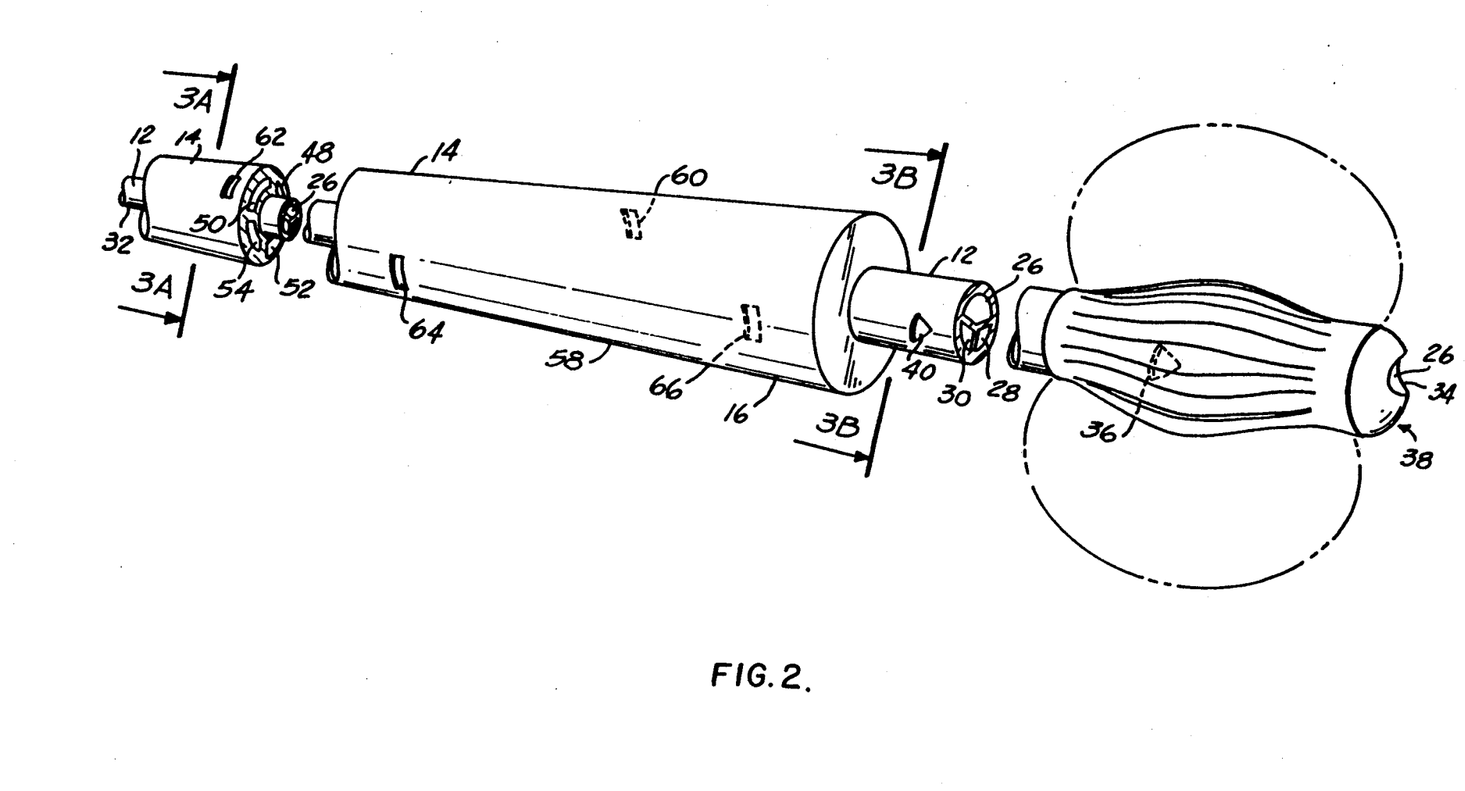
FIG. 2 is an isometric view of a number of segments of the catheter of FIG. 1.

Referring now to FIG. 1, a catheter 10 constructed in accordance with this invention is shown. As will be described in greater detail below, catheter 10 is easy to use, durable, simply constructed, and able to perform a variety of functions. In that regard, the embodiment of the catheter shown is designed for intravascular use to infuse therapeutic fluids, extract blood samples, provide electrical or optical communications between ends of the catheter, determine blood pressure, and determine cardiac output by Doppler ultrasound techniques.

As shown in FIG. 1, the catheter 10 includes an internal tube 12, external tube 14, ultrasound transducer 16, sensor 18, and termination assembly 20. The internal tube 12 and external tube 14 collectively define a catheter body that supports the other components and allows them to be positioned at desired locations within an intravascular conduit of a patient. The transducer 16 and sensor 18 obtain information from the patient for use in diagnosis and treatment, as will be described in greater detail below. The termination assembly 20 is coupled to both the internal tube 12 and external tube 14, and provides an interface between the catheter 10 and a control and processing system 22.

Addressing the various components of catheter 10 individually, the internal tube 12 is an elongate piece of flexible tubing having defined therein three lumens 26, 28, and 30. Tube 12 is preferably made of a standard medical grade flexible polyurethane having a hardness of Shore D65 and is roughly 115 centimeters long and 0.117 centimeter in diameter.

Lumens 26, 28, and 30 extend to the proximal end 32 of internal tube 12 and terminate at the termination assembly 20. Lumen 26 is known as a distal pressure lumen and extends from assembly 20, through the entire length of tube 12, to a distal pressure port 34.

Lumen 28 is known as a balloon lumen and extends from assembly 20 through the length of tube 12. Lumen 28 opens to the exterior of tube 12 at a balloon port 36 approximately five millimeters from the distal end 38 of tube 12. Finally, lumen 30 is known as a sensor lumen and also extends from assembly 20 through the length of tube 12. Lumen 30 opens to the exterior of tube 12 at a sensor port 40 about forty millimeters from the distal end 38 of tube 12.

Figure 3A:
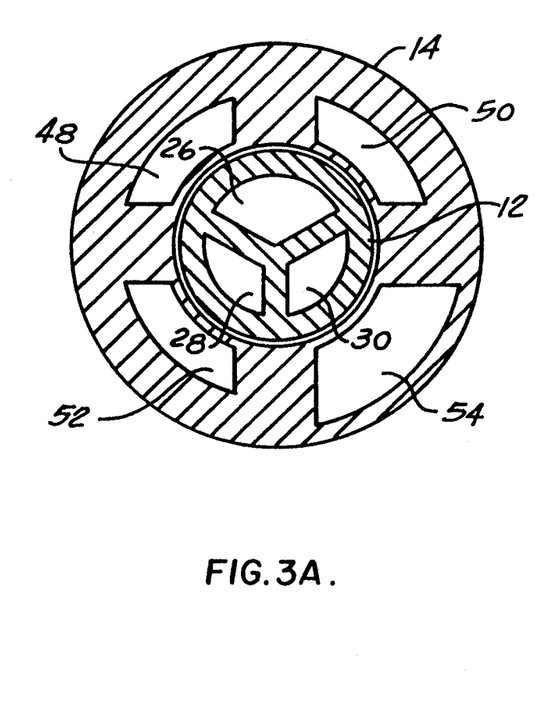
FIGS. 3A and 3B are sectional views of the catheter of FIGS. 1 and 2 along the section lines A—A' and B—B' of FIG. 2.
Figure 3B:
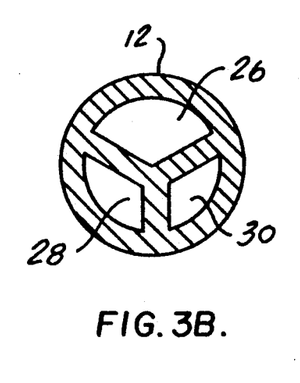

As shown in FIGS. 3A and 3B, lumens 26, 28, and 30 each define a circular sector when viewed in cross section. The distal pressure lumen 26 has the largest cross-sectional area (roughly 0.5 square millimeter). In contrast, the balloon and sensor lumens 28 and 30 are smaller in cross-sectional area (roughly 0.3 square millimeter each), but adequate for the assigned functions. The lumens 26, 28, and 30 are defined by walls of tube 12 that are of uniform thickness (roughly 0.125 millimeter).

From the foregoing, it is clear that tube 12 is provided with a relatively large number of usable lumens. Furthermore, when compared to conventional lumens of circular cross section provided in a catheter of the same diameter, each lumen 26, 28, and 30 has a relatively large cross-sectional area. For example, the distal pressure lumen 26 has a cross-sectional area comparable to that of the distal pressure lumen of a conventional eight French (2.67 millimeters in diameter) thermodilution catheter, despite the fact that the diameter of tube 12 is smaller (0.117 centimeter). This is an important advantage since it allows lumens having suitable pressure measurement characteristics to be included in a catheter having a diameter that is smaller than standard eight French devices.

The external tube 14 is an elongate piece of tubing and has five lumens 46, 48, 50, 52, and 54 provided therein. Tube 14, like tube 12, is made of a medical grade polyurethane, but has a hardness of Shore A93, making it relatively more flexible than the internal tube 12. The external tube 14 is roughly 105 centimeters long and 0.264 centimeter in diameter.

Addressing the various lumens 46, 48, 50, 52, and 54 individually, the center lumen 46 extends between the proximal end 56 and distal end 58 of tube 14 and is designed to receive the internal tube 12. Thus, as shown in FIG. 3A, the internal lumen 46 has a circular cross section and is slightly greater in diameter (roughly 0.122 centimeter) than the outer diameter of the internal tube 12. As shown in FIG. 1, internal tube 12 is longer than external tube 14 and extends from the distal end of internal lumen 46 by roughly 10 centimeters.

Lumens 48 and 50 are known as the first and second proximal pressure lumens, respectively. These lumens 48 and 50 begin at the termination assembly 20 at the proximal end 56 of tube 14. The first proximal pressure lumen 48 then extends the length of tube 14 and opens to the tube's exterior at a first proximal pressure port 60 located approximately five millimeters from the distal end 58 of tube 14. The second proximal pressure lumen 50 also extends the length of tube 14 and is open to the exterior of tube 14 at a second proximal pressure port 62 located roughly 180 millimeters from the distal end 58 of tube 14.

Lumens 52 and 54 are known as the injection and transducer lead lumens, respectively. These lumens 52 and 54 begin at the proximal end 56 of tube 14 at the termination assembly 20. The injection lumen 52 then extends the length of tube 14 and is open to the exterior of tube 14 at an injection port 64 located roughly 150 millimeters from the distal end 58 of tube 14. The transducer lead lumen 54 similarly extends the length of tube 14 and is open to the tube's exterior at a transducer lead port 66 located at the distal end 58 of tube 14.

As shown in FIG. 3A, lumens 48, 50, 52, and 54 each define a segment of an annulus in cross section. In that regard, the cross-sectional area of lumens 48, 50, and 52 is roughly 0.275 square millimeter each, while the cross-sectional area of lumen 54 is roughly 0.467 square millimeter to accommodate the transducer wiring. Lumens 48, 50, and 52 are spaced between the inner and outer surfaces of tube 14. Lumen 54 is also evenly spaced between the inner and outer surfaces of tube 14 but is approximately twice as large in cross section. As will be appreciated from FIG. 3A, with the internal tube 12 inserted in external tube 14, the size and location of the various lumens result in a substantially uniform wall thickness for lumens 48, 50, and 52.

Addressing now the transducer 16, transducer 16 may be any one of a variety of suitable transducer types, but is preferably of a cylindrical construction. The transducer 16 is located at the intersection of the internal tube 12 and the external tube 14 where it can be easily attached to tube 14 and the transducer wiring by a connector 70. As will be appreciated, the internal tube 12 can be positioned inside the external tube 14 before or after transducer 16 is attached without interference.

Figure 4:
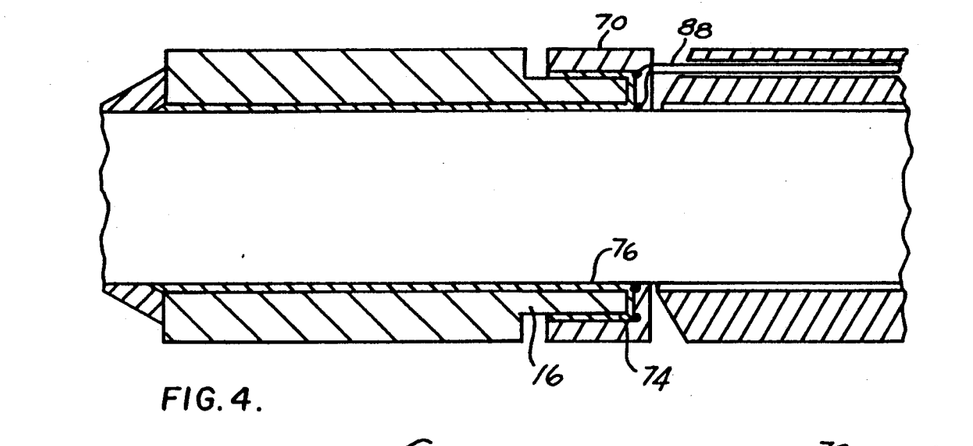
FIG. 4 is a sectional view of a segment of the catheter illustrating the connection of a transducer thereto.
Figure 5:
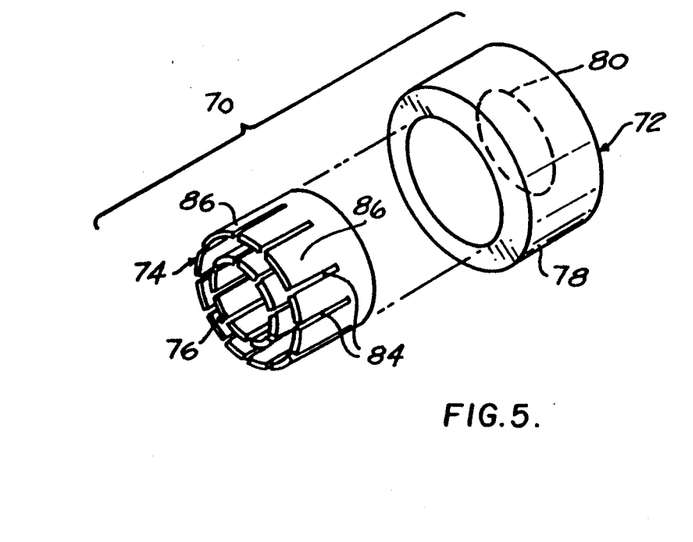
FIG. 5 is an exploded isometric view of a connector shown in FIG. 4.
Figure 6:
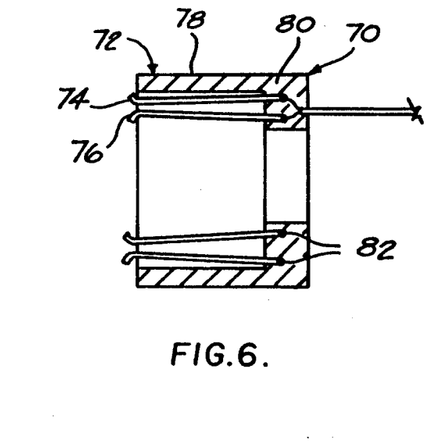
FIG. 6 is a sectional view of the connector of FIG. 5.

Turning now to a more detailed discussion of the construction of connector 70, reference is had to FIGS. 4, 5, and 6. As shown, the connector 70 includes three components: a plastic collar 72 and a pair of flexible conductive ring clips 74 and 76. The plastic collar 72 includes a cylindrical wall 78 coupled to a circular base 80. As shown in FIG. 5, the diameter of collar 72 is roughly equal to the diameter of transducer 16 and external tube 14.

The two coaxially aligned roughly cylindrical ring clips 74 and 76 have enlarged rims 82 that are molded into the circular base 80 of collar 72. As shown, the ring clips 74 and 76 are spaced apart at the collar 72 by a distance corresponding to the thickness t of the cylindrical transducer 16, but are slightly closer together at their projecting ends. Each ring clip 74 and 76 is interrupted by a plurality of circumferentially spaced-apart slots 84, to define a plurality of fingers 86, adding flexibility to the ring clips 74 and 76.

Because the projecting ends of the ring clips 74 and 76 are normally spaced apart by a distance less than the cylindrical main element thickness t, when an end of the transducer 16 is inserted between ring clips 74 and 76, they spread apart and apply a slight force to the cylindrical transducer 16 to maintain the desired electrical and mechanical interface. To further ensure this connection, some type of detent may also be used. As will be appreciated, a connector 70 constructed in this manner allows the desired mechanical and electrical connection to be easily and securely made to the transducer 16. Thus, the transducer 16 can be quickly removed and replaced as needed.

Addressing now the coupling of the two ring clips 74 and 76 of connector 70 to the transducer wiring 88, because a single cylindrical element 16 is employed, a coaxial cable provided in lumen 54 can be conveniently used for transducer wiring. More particularly, the internal conductor of cable 88 is coupled to the internal ring clip 76 of connector 70 by solder or a conductive adhesive and, thus, is coupled to the internal surface of transducer 16. Similarly, the external conductor of cable 88, commonly known as the grounding shield, is coupled to the external ring clip 74 of connector 70 by solder or a conductive adhesive and, thus, is coupled to an external surface of transducer 16. The use of coaxial cable 88 instead of conventional wires significantly enhances the overall flexibility of catheter 10.

The sensor 18 may be any one of a variety of devices including, for example, a thermistor or fiber-optic cell. Sensor 18 is preferably positioned adjacent the sensor port 40 on the internal tube 12. Sensor 18 is coupled to the termination assembly 20 by electrical wires or an optical fiber 90 located in lumen 30.

Turning now to a discussion of termination assembly 20, assembly 20 allows the various components of control and processing system 22 to be coupled to the catheter 10. The termination assembly 20 includes a plurality of flexible tubings 92, 94, 96, 98, and 100 coupled to the distal pressure lumen 26, balloon lumen 28, first proximal pressure lumen 48, second proximal pressure lumen 50, and injection lumen 52. The tubings 92, 94, 96, 98, and 100, respectively, end in a distal pressure connector 102, balloon connector 104, first proximal pressure connector 106, second proximal pressure connector 108, and thermal injection connector 110.

Tubings 92, 94, 96, 98, and 100 preferably have circular diameters and are slightly oversized with respect to their respective lumens. Connections are made by forcing each tubing into the corresponding lumen and then encapsulating the area. As a result, the connection is made fluid tight and a strain relief is formed.

The termination assembly 20 also includes a transducer connector 112 and sensor connector 114 connected to cable 88 and the electrical wires or optical fiber 90. As shown in FIG. 1, these portions of the termination assembly 20 are also encapsulated to relieve strain at the various component junctions.

Figure 7:
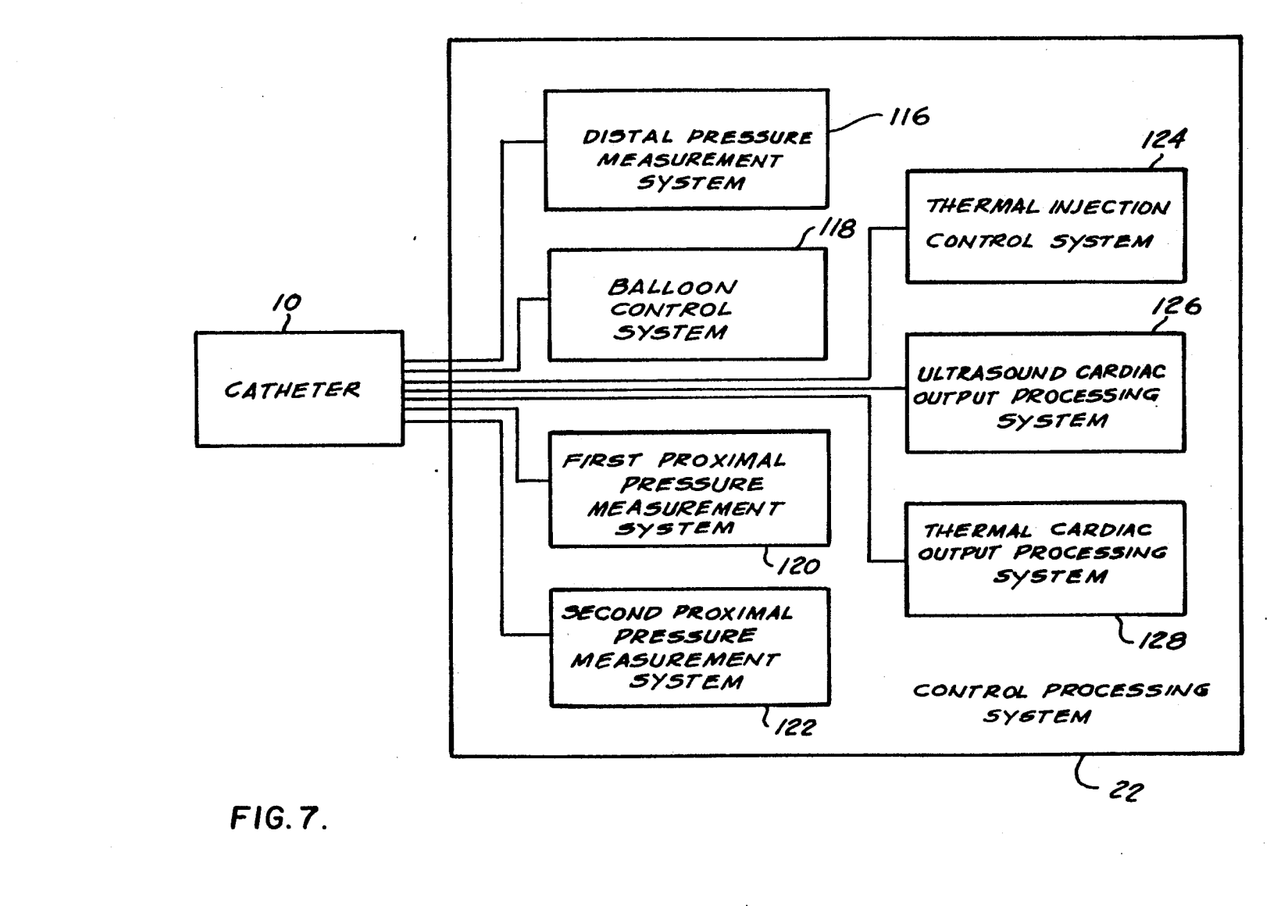
FIG. 7 is a block diagram illustrating a control and processing system used with the catheter of FIG. 1.

The termination assembly 20 is designed to interface with the control and processing system 22. In that regard, as shown in FIG. 7, the control and processing system 22 includes a distal pressure measurement system 16, balloon inflation/deflation device 118, first proximal pressure measurement system 120, second proximal measurement system 122, injection device 124, ultrasonic cardiac output processing system 126, and sensor monitoring system 128.

The distal pressure measurement device 116 is fluid coupled by connector 102 and tubing 92 to the distal pressure lumen 26 of internal tube 12. As a result, pressure in the intravascular conduit adjacent the distal pressure port 34 of catheter 10 is transmitted to the distal pressure measurement device 116 where an output is produced. Similarly, the first and second proximal pressure measurement systems 120 and 122 are coupled by connectors 106 and 108 to tubings 96 and 98. Thus, the first and second proximal pressure lumens 48 and 50 within external tube 14 are in fluid communication with the first and second proximal pressure measurement systems 120 and 122. As a result, fluid pressure in the intravascular conduit adjacent the first and second proximal pressure ports 60 and 62 is transmitted to systems 120 and 122, where outputs are produced.

The balloon inflation/deflation device 118, which may, for example, be a syringe, is selectably engagable with connector 104 of termination assembly 20 to introduce or withdraw gaseous fluid from lumen 28. Because lumen 28 is in fluidic communication with balloon 42, the injection of gaseous fluid into lumen 28 induces an expansion of balloon 42, while the withdrawal of gaseous fluid therefrom results in a retraction of balloon 42. In this manner, the volume of balloon 42 can be controlled by the health care provider.

As previously noted, the sensor 18 may be either a thermistor or a fiber-optic cell. With a thermistor employed as sensor 18, injection lumen 52 is coupled to the injection device 124 via the connector 110 provided in the termination assembly 20. During actual clinical use, a bolus of cold fluid is injected into the blood at port 64 via the injection lumen 52. The bolus is then swept past the thermistor 18, which produces an electrical signal in response to the changing temperature caused by the injection. This electrical signal is carried by the thermistor wires 90 in lumen 30 to the sensor-monitoring system 128. In this embodiment, system 128 is a thermal dilution cardiac output computer that monitors the temperature change over time to calculate the instantaneous cardiac output.

Alternatively, a fiber-optic cell may be employed as sensor 18 to monitor physical or chemical parameters of the fluid surrounding catheter 10. Lumen 30 now carries the fiber-optic strand or strands 90 that transceive optical signals between the cell 18 and the monitoring system 128. In this embodiment, system 128 is an optical computer that converts the optical signals into digital electronic signals that are, in turn, processed by a digital computer to produce the appropriate readouts of the physical or chemical parameters being monitored. As will be appreciated, unlike the thermal dilution application discussed above, the injection lumen 52 is now available for the infusion of therapeutic fluids.

Finally, an ultrasonic cardiac output-processing system 126 is coupled by connector 110 of termination assembly 20 to the coaxial cable 88 and, hence, the ultrasound transducer 16. The transducer responds to electrical pulses from cable 88 by emitting ultrasonic energy. Ultrasonic energy reflected by the flowing blood is, in turn, transformed into electrical signals by the transducer 16. These signals are transmitted by coaxial cable 88 to system 126. The ultrasonic cardiac output-processing system 126 determines the Doppler frequency shift induced by the flowing blood and uses that information to compute blood flow.

Addressing now the overall operation of catheter 10, the distal end of catheter 10 is inserted into an appropriate blood vessel and balloon 42 inflated. In this manner, catheter 10 is advanced until it passes through the superior vena cava, the right atrium, the tricuspid valve, the right ventricle, and into the main pulmonary artery. During the advancement of the catheter 10, pressure at the distal pressure port 34, first proximal pressure port 60, and second proximal pressure port 62 may be measured via systems 116, 120, and 122 to assist in positioning of the catheter within the pulmonary artery. In addition, the Doppler signals produced by transducer 16 will be analyzed by the ultrasonic cardiac output-processing system 126 to provide an output that is position dependent. The catheter 10 will then be advanced until the outputs of all four systems indicate that the desired position in the pulmonary artery has been reached.

At this time, the cardiac output-processing techniques described above may be employed to continuously determine cardiac output. In addition, the sensor 18 may also be used to produce an output indicative of the physical or chemical parameters it senses.

The catheter 10 described above has a number of advantages over conventional catheter designs. In that regard, catheter 10 has an extremely high lumen count for its size. More particularly, catheter 10 is able to provide seven lumens for intravascular applications in which the catheter 10 has an outer diameter of 0.26 centimeter. The ability to achieve such a high lumen count is a function of the geometry adopted for both the lumens and catheter.

In addition to having a high lumen count, catheter 10 also allows the lumens to have relatively large cross-sectional areas. As will be appreciated, this is particularly important in applications in which the lumens are required for fluid communication without obstruction. This is especially true for lumens used to communicate pressure changes for use in pressure measurement.

The stepped, dual-diameter coaxial construction of catheter 10 is also advantageous. More particularly, if catheter 10 had a uniform diameter over its entire length, the transducer 16 would necessarily project from the catheter surface. With the transducer 16 projecting from the surface of catheter 10, transducer 16 would be exposed to a greater risk of thrombus formation and would potentially introduce variations into the flow of fluid across the catheter 10. By employing the internal tube 12 and external tube 14 to produce a catheter 10 having a stepped configuration, however, a cylindrical transducer 16 can be easily added to the end of the external tube 14, before or after the internal and external tubes 12 and 14 are joined, overcoming these limitations. The use of connector 70 further simplifies the attachment of transducer 16 to tube 14.

The catheter 10 is also constructed to ensure roughly uniform flexibility the entire length of the catheter 10. In that regard, internal tube 12 is made of a more rigid material than external tube 14. Thus, although internal tube 12 has a comparatively small diameter, it will retain a significant portion of the rigidity exhibited by the external tube 14. As a result, the internal tube 12 resists a tendency to collapse upon insertion, making catheter 10 easier to introduce into the patient's vascular system.

Finally, the catheter 10 is constructed to be relatively flexible. Conventional catheters were limited by the relatively stiff wiring used in connection with sensors carried by the catheters. As described above, however, the disclosed catheter 10 employs a single cylindrical ultrasound transducer 16 allowing a single coaxial cable 88 to be easily employed. With a braided external conductor and a thin internal conductor, coaxial cable 88 is quite flexible. Thus, the overall flexibility of the catheter 10 is improved.

Those skilled in the art will recognize that the embodiments of the invention disclosed herein are exemplary in nature and that various changes can be made therein without departing from the scope and spirit of the invention. In this regard, the invention is readily embodied for use in a variety of conduits and for use with various types of ultrasound transducers 16. Further, it will be recognized that the applications employed for the various lumens, as well as the components of the termination assembly 20 and control and processing system 22 can be varied. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A catheter comprising:
    an external tube having proximal and distal ends and being provided with a primary lumen and a plurality of secondary lumens, said primary lumen being roughly circular in cross section and each said secondary lumen roughly defining a segment of an annulus in cross section; and
    an internal tube having proximal and distal ends and being provided with a plurality of internal tube lumens, each said internal tube lumen roughly defining a circular sector in cross section, said internal tube being received within said primary lumen of said external tube.

2. The catheter of claim 1, further comprising:
    a sensor coupled to said internal tube; and
    communication means, received within one of said internal tube lumens and connectable to said sensor for communication with said sensor.

3. The catheter of claim 2, wherein said sensor comprises a thermistor and said communication means comprises an electrical conductor.

4. The catheter of claim 2, wherein said sensor comprises an optical cell and said communication means comprises an optical fiber.

5. A method of producing a catheter comprising the steps of:
    producing an external tube, having proximal and distal ends, a primary lumen, and a plurality of secondary lumens, said primary lumen being roughly circular in cross section and each said secondary lumen roughly defining a segment of an annulus in cross section; and
    producing an internal tube in said primary lumen of said external tube, said internal tube having a plurality of internal tube lumens, each said internal tube lumen roughly defining a circular section in cross section.

* * * * *

UNITED STATES PATENT AND TRADEMARK OFFICE
CERTIFICATE OF CORRECTION

PATENT NO. : 5,286,259  
DATED : February 15, 1994  
INVENTOR(S) : D. Ganguly et al.

Page 1 of 5

It is certified that error appears in the above-indentified patent and that said Letters Patent is hereby corrected as shown below:

COLUMN    LINE

[56]           Ref. 15        Please add --3,347,224  10/1967  Adams--  
"U.S. Patents"

[56]           Ref. 16        Please add --3,359,974  12/1967  Khalil--  
"U.S. Patents"

[56]           Ref. 17        Please add --3,430,625  3/1969  McLeod, Jr.--  
"U.S. Patents"

[56]           Ref. 18        Please add --3,443,433  5/1969  Liston et al.--  
"U.S. Patents"

[56]           Ref. 19        Please add --3,448,739  6/1969  Stark et al.--  
"U.S. Patents"

[56]           Ref. 20        Please add --3,499,435  03/1970  Rockwell et al.--  
"U.S. Patents"

[56]           Ref. 21        Please add --3,542,014  11/1970  Peronneau--  
"U.S. Patents"

[56]           Ref. 22        Please add --3,661,148  5/1972  Kolin--  
"U.S. Patents"

[56]           Ref. 23        Please add --3,707,960  01/1973  Freed--  
"U.S. Patents"

[56]           Ref. 24        Please add --3,726,269  4/1973  Webster, Jr.--  
"U.S. Patents"

UNITED STATES PATENT AND TRADEMARK OFFICE
CERTIFICATE OF CORRECTION

PATENT NO. : 5,286,259
DATED : February 15, 1994
INVENTOR(S) : D. Ganguly et al.

It is certified that error appears in the above-indentified patent and that said Letters Patent is hereby corrected as shown below:

COLUMN     LINE

[56] "U.S. Patents"     Ref. 25     Please add --3,798,967 03/1974 Gieles et al.--

[56] "U.S. Patents"     Ref. 26     Please add --3,838,683 10/1974 Kolin--

[56] "U.S. Patents"     Ref. 27     Please add --3,901,077 08/1975 McCarty et al.--

[56] "U.S. Patents"     Ref. 28     Please add --3,938,502 02/1976 Bom--

[56] "U.S. Patents"     Ref. 29     Please add --3,951,136 04/1976 Wall--

[56] "U.S. Patents"     Ref. 30     Please add --3,985,123 10/1976 Herzlinger et al.--

[56] "U.S. Patents"     Ref. 31     Please add --4,024,873 05/1977 Antoshkiw et al.--

[56] "U.S. Patents"     Ref. 32     Please add --4,105,022 08/1978 Antoshkiw et al.--

[56] "U.S. Patents"     Ref. 33     Please add --4,142,412 03/1979 McLeod et al.--

[56] "U.S. Patents"     Ref. 34     Please add --4,232,373 11/1980 Jackson et al.--

UNITED STATES PATENT AND TRADEMARK OFFICE
CERTIFICATE OF CORRECTION

PATENT NO. : 5,286,259
DATED : February 15, 1994
INVENTOR(S) : D. Ganguly et al.

It is certified that error appears in the above-indentified patent and that said Letters Patent is hereby corrected as shown below:

COLUMN    LINE

| | | |
|---|---|---|
| [56] "U.S. | Ref. 35 Patents" | Please add --4,237,729 12/1980 McLeod et al.-- |
| [56] "U.S. | Ref. 36 Patents" | Please add --4,259,870 04/1981 McLeod et al.-- |
| [56] "U.S. | Ref. 37 Patents" | Please add --4,295,464 10/1981 Shihata-- |
| [56] "U.S. | Ref. 38 Patents" | Please add --4,299,226 11/1981 Banka-- |
| [56] "U.S. | Ref. 39 Patents" | Please add --4,319,580 03/1982 Colley et al.-- |
| [56] "U.S. | Ref. 40 Patents" | Please add --4,329,993 05/1982 Lieber et al.-- |
| [56] "U.S. | Ref. 41 Patents" | Please add --4,333,352 06/1982 Connery et al.-- |
| [56] "U.S. | Ref. 42 Patents" | Please add --4,354,502 10/1982 Colley et al.-- |
| [56] "U.S. | Ref. 43 Patents" | Please add --4,397,191 08/1983 Forden-- |
| [56] "U.S. | Ref. 44 Patents" | Please add --4,459,853 07/1984 Miwa et al.-- |

UNITED STATES PATENT AND TRADEMARK OFFICE
CERTIFICATE OF CORRECTION

PATENT NO. : 5,286,259  
DATED : February 15, 1994  
INVENTOR(S) : D. Ganguly et al.

Page 4 of 5

It is certified that error appears in the above-indentified patent and that said Letters Patent is hereby corrected as shown below:

COLUMN      LINE

[56] "U.S. Patents"         Ref. 45         Please add --4,563,181  01/1986  Wijayarathna et al.--

[56] "U.S. Patents"         Ref. 46         Please add --4,566,460  01/1986  Sato et al.--

[56] "U.S. Patents"         Ref. 47         Please add --4,582,067  04/1986  Silverstein et al.--

[56] "U.S. Patents"         Ref. 48         Please add --4,637,389  01/1987  Heyden--

[56] "U.S. Patents"         Ref. 49         Please add --4,637,401  01/1987  Johnston--

[56] "U.S. Patents"         Ref. 50         Please add --4,674,336  06/1987  Johnston--

[56] "U.S. Patents"         Ref. 51         Please add --4,950,257  08/1990  Hibbs et al.--

[56] "Foreign Patents"      Ref. 4          Please add --2758039  07/1979  Germany--

[56] "Foreign Patents"      Ref. 5          Please add --288833-A  11/1988  European--

[56] "Foreign Patents"      Ref. 6          Please add --605608  04/1978  Russia--

UNITED STATES PATENT AND TRADEMARK OFFICE
CERTIFICATE OF CORRECTION

PATENT NO. : 5,286,259
DATED : February 15, 1994
INVENTOR(S) : D. Ganguly et al.

It is certified that error appears in the above-indentified patent and that said Letters Patent is hereby corrected as shown below:

| COLUMN | LINE | |
|---|---|---|
| [56] "Other Publications" | Ref. 1 | Please add --Martin, R.W., et al. "An Ultrasonic Catheter for Intravascular Measurement of Blood Flow: Technical Details," Transactions on Sonics and Ultrasonics, Vol. Su-27, No. 6 (November 1980), pp. 277-286.-- |
| [56] "Other Publications" | Ref. 2 | Please add --Olson, R., et al., "A Nondestructive Ultrasonic Technique to Measure Diameter and Blood Flow in Arteries," IEEE Transactions on Biomedical Engineering, Vol. BME-21, No. 2 (March 1974), pp. 168-171.-- |
| [56] "Other Publications" | Ref. 3 | Please add --Wells, P.N.T., "Doppler Methods," Biomedical Ultrasonics, (1977), pp. 354-357.-- |
| 1 | 45 | "car" should read --care-- |
| 3 | 11 | "crosssection" should read --cross section-- |
| 7 | 19 &20 | "sys-tem 16" should read --system 116-- |

Signed and Sealed this

Nineteenth Day of July, 1994

Attest:

BRUCE LEHMAN

*Attesting Officer*          *Commissioner of Patents and Trademarks*